United States Patent [19]

Kanno et al.

[11] Patent Number: 4,588,927
[45] Date of Patent: May 13, 1986

[54] LIGHT SUPPLY APPARATUS FOR AN ENDOSCOPE

[75] Inventors: Masahide Kanno; Atsushi Amano; Seiichi Hosoda; Shinichiro Hattori, all of Tokyo, Japan

[73] Assignee: Olympus Optical Co., Ltd., Tokyo, Japan

[21] Appl. No.: 635,243

[22] Filed: Jul. 27, 1984

[30] Foreign Application Priority Data

Aug. 5, 1983 [JP] Japan .................................. 58-143549

[51] Int. Cl.⁴ .............................................. H01K 7/00
[52] U.S. Cl. ...................................... 315/307; 128/6.0; 315/76; 315/291; 604/67
[58] Field of Search ........................ 315/76, 307, 291; 128/4.0, 6.0; 604/67

[56] References Cited

U.S. PATENT DOCUMENTS

| | | | |
|---|---|---|---|
| 4,343,300 | 8/1982 | Hattori | 128/6 |
| 4,359,670 | 11/1982 | Hosaka et al. | 315/307 |
| 4,503,841 | 3/1985 | Tsukaya et al. | 128/4 |
| 4,527,093 | 7/1985 | Yamauchi et al. | 315/307 |
| 4,532,936 | 8/1965 | Leveen | 604/67 |

*Primary Examiner*—Harold Dixon

[57] ABSTRACT

A light supply apparatus for an endoscope comprises a discharge lamp for supplying light to an endoscope, and a microprocessor for controlling various devices such as a display unit for displaying data. The discharge lamp is ignited by an ignition signal. The microprocessor is reset by the ignition signal. The display unit is held in the same state as before the ignition of the lamp even when the microprocessor is reset.

6 Claims, 5 Drawing Figures

LIGHT SUPPLY APPARATUS FOR AN ENDOSCOPE

BACKGROUND OF THE INVENTION

The present invention relates to a light supply apparatus, more particularly a light supply apparatus for use in an endoscope.

A light supply apparatus using an endoscope with a discharge lamp as the light source may erroneously actuate a peripheral circuit. That is, the ignition noise generated at the start of the lamp may make a CPU overrun, which erroneously selects and actuates a peripheral circuit, i.e., a display circuit, an aperture drive circuit, a pump drive circuit or the like. To avoid this error, the CPU and peripheral circuits are reset during the ignition period of the discharge lamp. Once the display circuit has been reset, the display member on the panel of the light supply apparatus is de-energized to display nothing. This makes the operator feel uneasy. Further, once peripheral circuits have been reset, the values preset to these circuits are cleared. Therefore, these values must be set again after the discharge lamp is ignited.

SUMMARY OF THE INVENTION

The object of the present invention is to provide a light supply apparatus for an endoscope, which enables the peripheral circuits of a microprocessor to maintain the preset values even when a discharge lamp is ignited.

According to this invention, there is provided a light supply apparatus for an endoscope, comprising a light source for supplying light to the endoscope, a detector for detecting the ignition of this light source, a microprocessor for controlling the various circuits included in the endoscope, a circuit for resetting the microprocessor, and a circuit for causing said various circuits to maintain the preset values when the discharge lamp is ignited.

DETAILED DESCRIPTION OF THE PREFERRED EMBODIMENT

Figure 1:
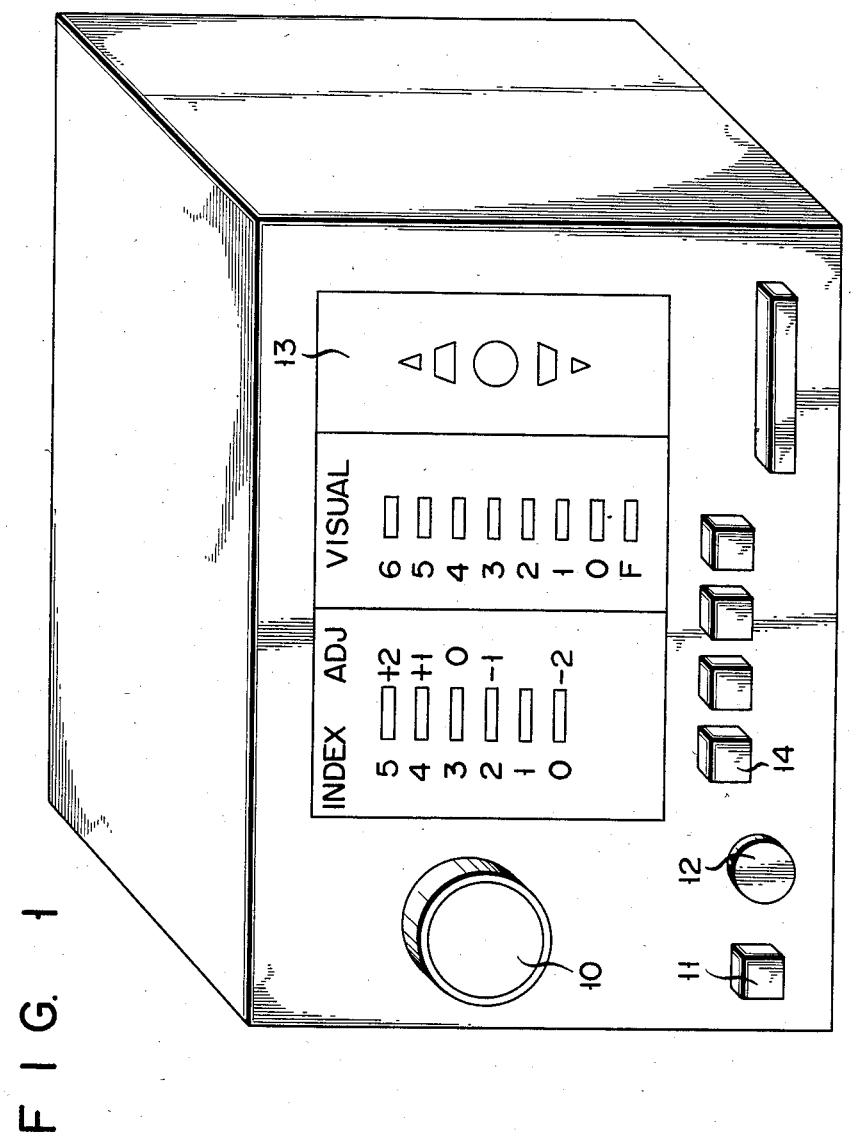
FIG. 1 is a perspective view of a light supply apparatus according to one embodiment of the present invention.

As shown in FIG. 1, the light supply apparatus according to the invention comprises a scope socket 10, a power switch 11, a lamp switch 12 and an LED display panel 13. The connector of an endoscope (not shown) may be coupled to the scope socket 10.

Figure 2:
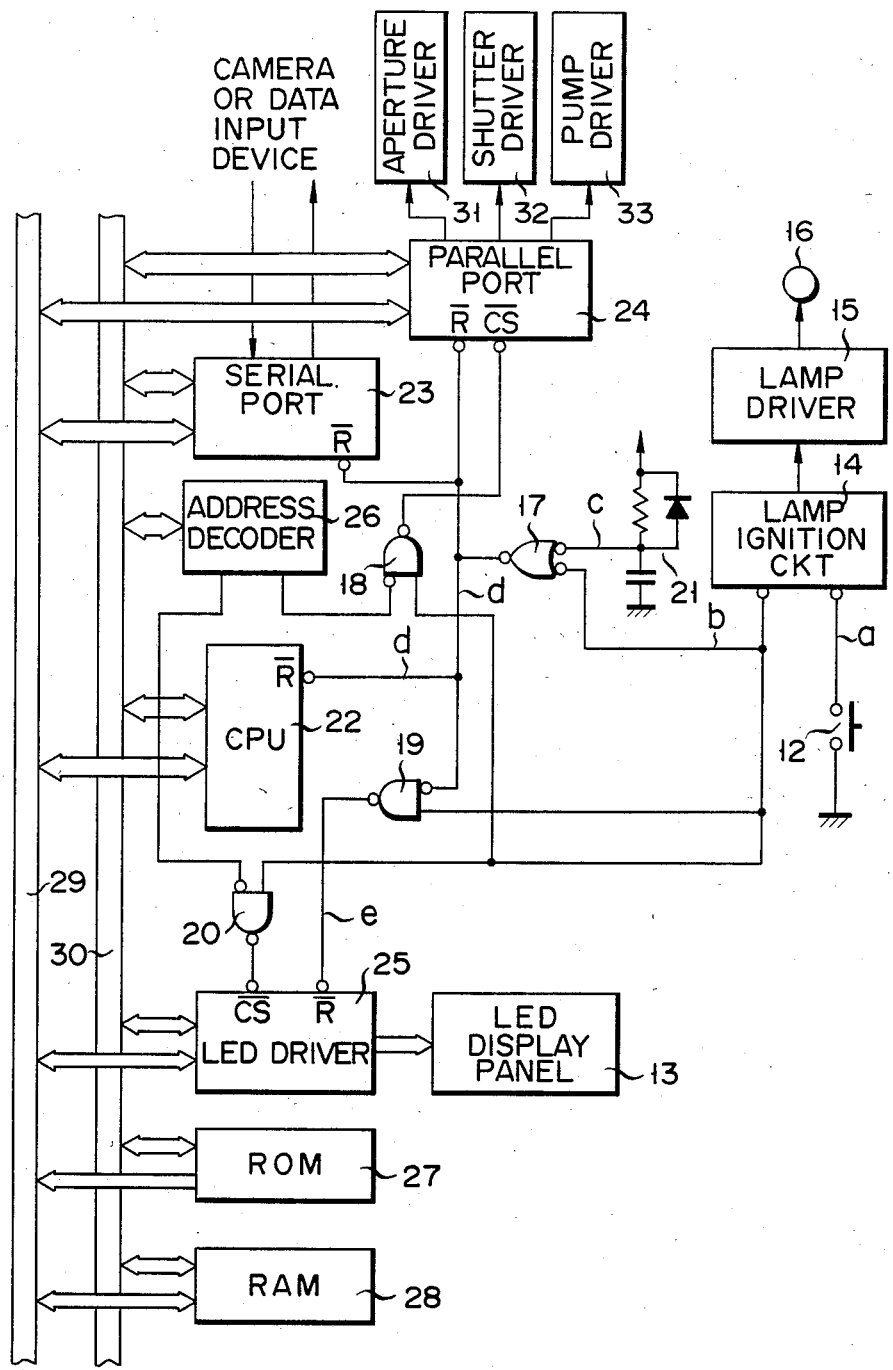
FIG. 2 is a circuit diagram of the light supply apparatus shown in FIG. 1.

As illustrated in FIG. 2, the lamp switch 12 is used to connect a lamp ignition circuit 14 to an input terminal. The output terminal of the lamp ignition circuit 14 is connected to a lamp drive circuit 15, which in turn is connected to a discharge lamp 16, i.e., a light source. The circuit 14 has another output terminal which is connected to one input terminal of an OR gate 17, one input terminal of an AND gate 18, one input terminal of an AND gate 19 and one input terminal of an AND gate 19. A reset circuit 21 is coupled to the other input terminal of the OR gate 17. The output terminal of the OR gate 17 is connected to the other input terminal of the AND gate 19, the reset terminal $\overline{R}$ of a CPU 22 (i.e., a microprocessor), the reset terminal $\overline{R}$ of a serial port 23, and the reset terminal $\overline{R}$ of a parallel port 24. The output terminal of the AND gate 19 is coupled to the reset terminal $\overline{R}$ of an LED driver 25. The output terminal of the address decoder is connected to the other input terminal of the AND gate 18 and also to the other input terminal of the AND gate 20. The output terminals of the AND gates 18 and 20 are connected to the chip selection terminals $\overline{CS}$ of the port 24 and LED driver 25, respectively. The output section of the LED driver 25 is coupled to the LED display panel 13. A ROM 27 is provided which stores the program for controlling the light supply apparatus. A RAM 28 is provided to store and supply various data. The serial port 23, parallel port 24, LED driver 25, ROM 27 and RAM 28 are connected by a data bus 29 and an address bus 30 to the CPU 22. The serial port 23 is connected to a camera (not shown) or to a data input device (not shown).

Figure 3:
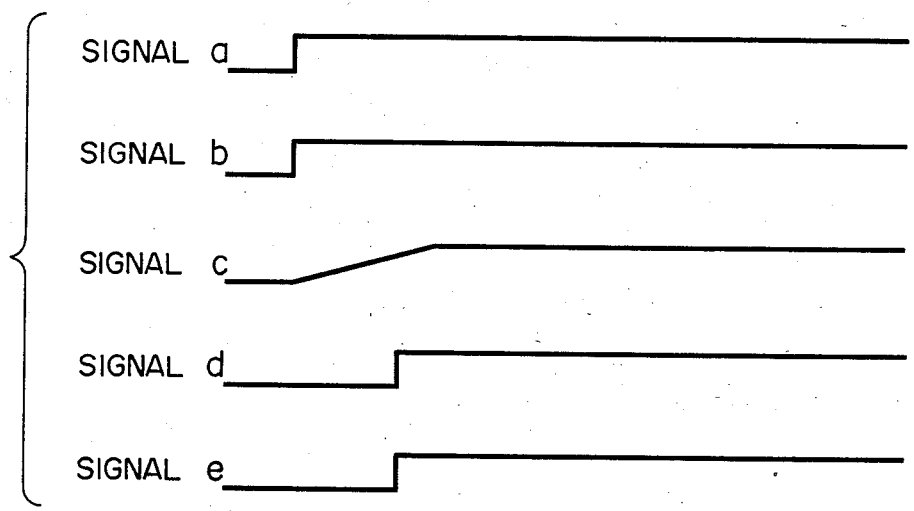
FIG. 3 and FIG. 4 are timing charts of signals, illustrating how the circuit of FIG. 2 operates.

The operation of the circuit shown in FIG. 2 will now be described with reference to the timing charts of FIGS. 3 and 4. When the power switch 11 is turned on, the input terminal of the lamp ignition circuit 14 has a signal a and a signal c, whose level gradually rises as shown in FIG. 3, is supplied to the OR gate 17. The output signal d of the OR gate 17 is at the low level when the power switch 11 is turned on. The CPU 22, serial port 23 and parallel port 24 are therefore reset. At the same time, the LED driver 25 is reset since the output signal e of the AND gate 19 is at a low level when the switch 11 is turned on. When the signal c reaches a predetermined level, the output signal d of the OR gate 17 rises to a high level, whereby the reset states of the CPU 22, serial port 23 and parallel port 24 are released. As a result, the output signal e of the AND gate 19 rises to a high level. The LED driver 25 is therefore released from the reset state. The CPU 22 starts controlling the communication between a camera (not shown) and a data input device (not shown). Under the control of the CPU 22 the aperture and shutter of the camera, a pump (not shown) and the LED display panel 13 are actuated in accordance with the data transferred via the data bus 29.

Figure 4:
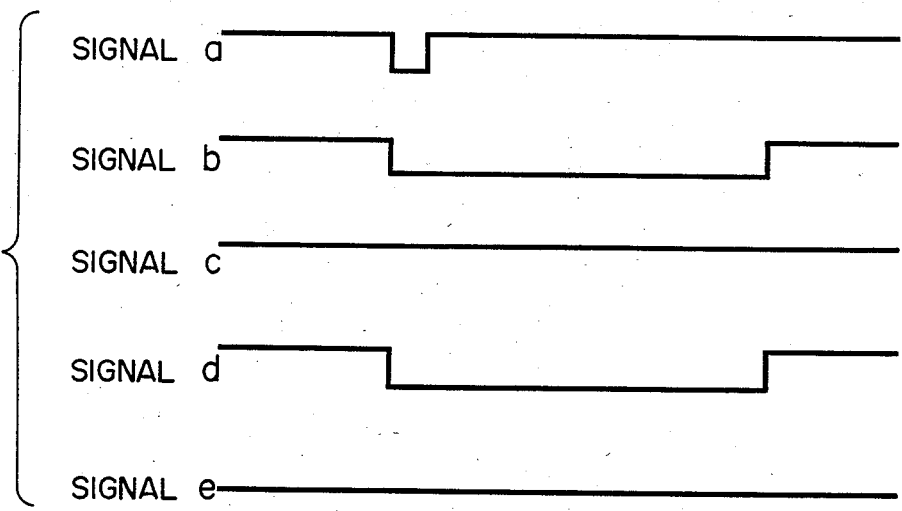

When the lamp switch 12 is turned on, a signal a shown in FIG. 4 is input to the lamp ignition circuit 14. In response to this signal a, the circuit 14 lowers the level of the signal b. This low-level signal b is supplied as an ignition signal to the lamp drive circuit 15. The ignition signal is also input to the OR gate 17, thus lowering the output signal d of the OR gate 17 to the low level. The CPU 22, serial port 23 and parallel port 24 are therefore reset. The output signal e of the AND gate 19 remains at a high level, nonetheless. The LED driver 25 is not therefore reset. The output signal of the AND gate 20, i.e., the signal supplied to the chip selection terminal $\overline{CS}$ of the LED driver 25, rises to a high level. Consequently, the LED driver 25 is not selected. That is, the LED display panel 13 stays in the same state as when the lamp switch 13 is turned on.

The lamp drive circuit 15 ignites the discharge lamp 16 in response to the ignition signal. The light emitted from the lamp 16 is guided by a light guide (not shown) of the endoscope. When the discharge lamp 16 is ignited, the output signal b of the lamp ignition circuit 14 rises to a high level. As a result, the output signal d of the OR gate 17 rises to a high level, whereby the CPU 22, serial port 23 and parallel port 24 are no longer reset. The CPU 22 therefore controls an aperture driver 31, a shutter driver 32 and a pump driver 33. These drivers 31, 32 and 33 are thus actuated in accordance with the data supplied via the data bus 29 and a parallel port 24. At this time, the signal supplied to the first input terminal of the AND gate 20 is at a high level. The LED driver 25 may therefore be selected in accordance with the level of the output signal of the address decoder 26. If the LED driver 25 is selected, the data displayed by the LED display panel 13 will be changed.

Figure 5:
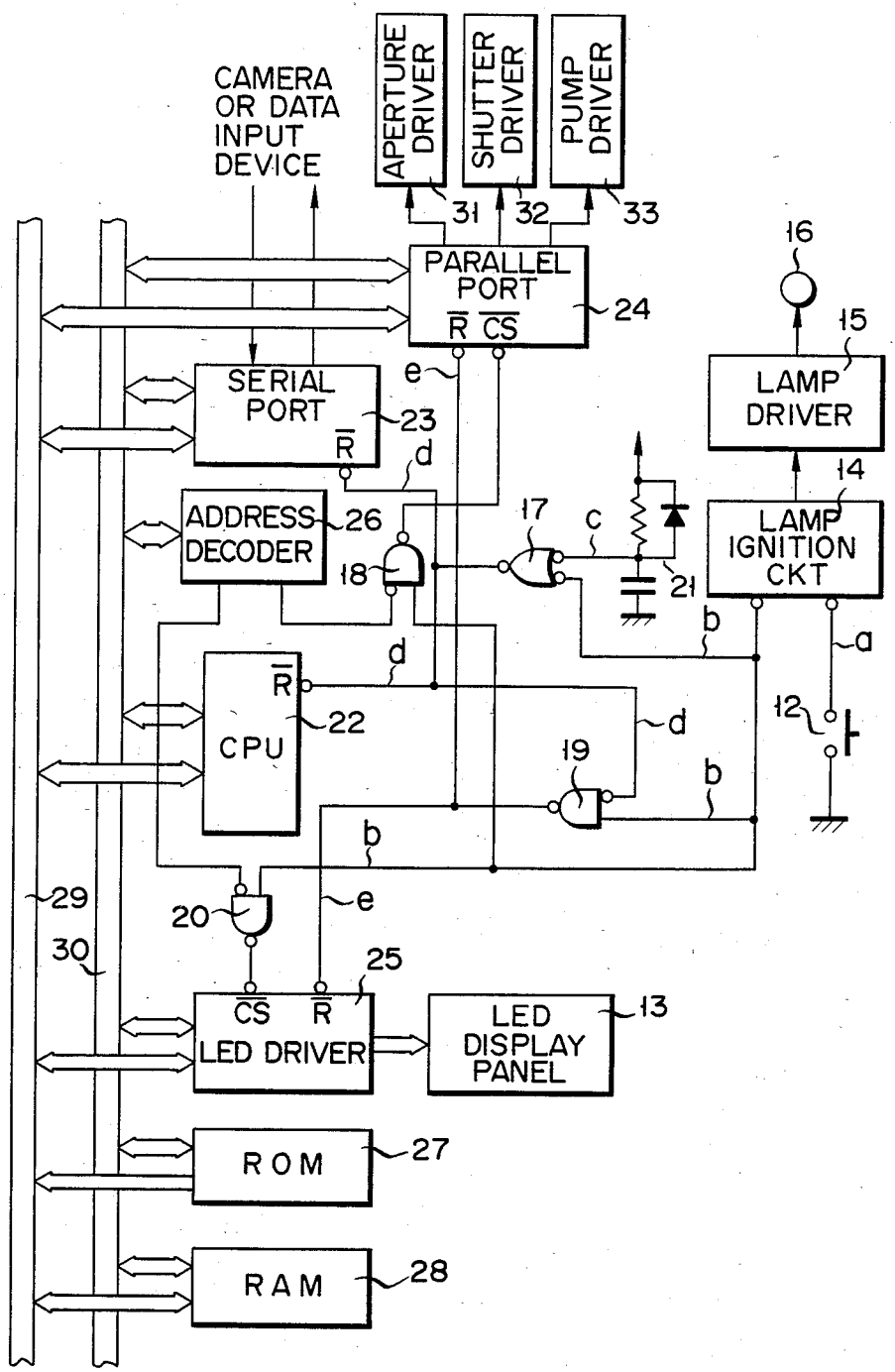
FIG. 5 is a circuit diagram of the light supply apparatus according to the other embodiment.

When the reset terminal $\overline{R}$ of the parallel port 24 is coupled to the output terminal of the AND gate 19 instead of to the output terminal of the OR gate 17, as shown in FIG. 5, the port 24 will not be reset even if the lamp switch 12 is turned on. This is because the reset terminal R of the port 24 is at a low level and because the output signal of the AND gate 18 (i.e., the input signal of the chip selection terminal $\overline{CS}$ of the port 24) is at a high level, and therefore, the parallel port 24 is not selected. That is, the parallel port 24 can hold the drivers 31, 32 and 33 in the same state as before the ignition of the lamp 16 in accordance with the output signal of the AND gate 18 even if the lamp switch 12 is turned on while the drivers 31, 32 and 33 are operating, and the lamp ignition circuit 14 supplies an iginition signal to the lamp drive circuit 15, thereby igniting the discharge lamp 16.

As described above, according to the present invention, the microprocessor is reset when the light source lamp is ignited, so as not to overrun due to the ignition noise, and the peripheral circuits, i.e., the display circuit, aperture drive circuit, pump driver and the like, are held in the same state as before the ignition, nonetheless. Therefore, the operator never feels uneasy due to an interrupted display and need not set the values in the peripheral circuits after every ignition of the light source lamp.

What is claimed is:

1. A light supply apparatus for an endoscope, comprising:

light source means for supplying light to an endoscope;
    light source igniting means for igniting said light source means;
    ignition detecting means for detecting the ignition of said light source means;
    display means for displaying various data;
    a microprocessor for controlling said display means and various driver means;
    reset means for resetting the microprocessor when said ignition detecting means detects the ignition of the light source means; and
    means responsive to the detection of ignition for maintaining at least said display means in the same state as before the ignition of the light source means.

2. A light supply apparatus according to claim 1, wherein said light source igniting means comprises a lamp switch to be operated to ignite said light source means and ignition signal generating means for generating an ignition signal in response to the operation of the lamp switch, and said ignition detecting means comprises means for supplying a reset signal to said microprocessor in response to the said ignition signal.

3. A light supply apparatus according to claim 2, wherein said reset means comprises logic gate means for receiving said ignition signal and a signal generated upon the start of power supply and gradually rising to a high level, said logic gate means generating the reset signal in response to the start of ignition and power on.

4. A light supply apparatus according to claim 2, wherein said responsive means comprises a logic gate means which receives the signals from said ignition detecting means and ignition means and which supplies a reset signal to said display means in response to said reset signal and a constant signal in response to said ignition signal thereto.

5. A light supply apparatus according to claim 1, wherein said various driver means are an aperture driver, a shutter driver for driving the shutter of the light source means, and a pump driver for driving a pump.

6. A light supply apparatus according to claim 1, wherein said light source means is a discharge lamp.

* * * * *